United States Patent [19]

Jacobsen

[11] Patent Number: Plant 6,602

[45] Date of Patent: Feb. 14, 1989

[54] GERANIUM PLANT NAMED PINK SILVER CROWN

[76] Inventor: Peter Jacobsen, P.O. Box 2, Hyde Park, Ontario, Canada

[21] Appl. No.: 89,519

[22] Filed: Aug. 26, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A geranium plant named Pink Silver Crown, characterized by its pink flower color, variegated green and white leaves, short leaf internodes, good branching, and compact growth habit.

1 Drawing Sheet

The present invention comprises a new and distinct cultivar of geranium named Pink Silver Crown. The new geranium is of the botanical species *Pelargonium peltatum,* commonly referred to as an ivy geranium characterized by its trailing growth habit and generally ivy-shaped leaves.

Pink Silver Crown is a sport discovered by applicant in a controlled environment in Hyde Park, Ontario, Canada in February 1984. The parent was a trailing ivy geranium which has pink flowers, green non-variegated leaves, and long internodes. The precise identification and name of the parent cultivar are not known at this time. Pink Silver Crown was discoverd as one flowering plant within a bed of parent plants.

The first act of asexual reproduction of Pink Silver Crown was accomplished when vegetative cuttings were taken in April, 1984 in a controlled environment in Hyde Park, Ontario, Canada by a technician working under formulations established and supervised by applicant. Horticultural examination of selected units initiated in October, 1984 has demonstrated that the combination of characteristics as herein disclosed for Pink Silver Crown are firmly fixed and are retained through sucessive generations of asexual reproduction. Pink Silver Crown has not been observed under all possible environmental conditions. The phenotype may vary significantly with variations in environment such as temperature, light intensity, and day length. The following observations, measurements, and comparisons describe plants grown in Hyde Park, Ontario, Canada under conditions which approximate those generally used in commercial practice.

The following traits have been repeatedly observed and are determined to be basic characteristics of Pink Silver Crown, which in combination distinguish this geranium as a new and distinct cultivar.

1. Variegated leaf which consists of a white margin, a medium green center, and a light green zone intermediate the center and the margin.
2. Short leaf internodes.
3. Pink flower color.
4. Compact growth habit.
5. Fast rooting.
6. No growth treatment is necessary for quality plant production.
7. Good branching.

Of the many commercial cultivars known to the present inventor, the most similar in comparison to Pink Silver Crown are Pink-Mini-Cascade and Pink Cascade. Reference is made to attached Chart A which compares certain characteristics of Pink Silver Crown to those same characteristics of Pink-Mini-Cascade and Pink Cascade. The measurements and comparative information appearing on Chart A was based on twelve (12) separate plants of each of the compared cultivars, with the numbers appearing being the average of the twelve measurements. Generally, in comparison to Pink-Mini-Cascade, Pink Silver Crown has variegated leaves, longer internodes, and less branching. In comparison to Pink Cascade, Pink Silver Crown has variegated leaves, shorter internodes, and better branching. The flower color of all of the compared varieties is approximately the same.

The accompanying photographic drawing shows typical flower and foliage characteristics of Pink Silver Crown. The photograph is in black and white, with a complete flower and several leaves being colored to accurately depict flower and foliage colors.

In the following description color references are made to The Royal Horticultural Society Colour Chart. The color values were determined between 2:20 and 2:40 p.m. on June 24, 1986 under diffused light at Hamilton, Canada.

Classification:

*Botanical.—Pelargonium peltatum.*

*Commercial.*—Ivy geranium, cv. Pink Silver Crown.

INFLORESCENCE

A. Umbel:

*Average diameter.* 66 mm.

*Average depth.* 50 mm.

*Peduncle length.* 106 mm.

*Pedicel length.*—32 mm.

B. Corolla:

*Average diameter.*—39 mm.

*Form.*—5 petal single; nearly round.

*Color.*—Upper surface: The top 2 petals are perceptively a more vivid pink 55A than the bottom three petals which are approximately 54B. Under surface: slightly lighter than values noted above.

C. Bud: Elongated, elliptical in shape

D. Reproductive organs:

*Androecium.*—6 stamens.

*Gynoecium.*—5 lobes on stigma, color red; style light pink in color.

E. Spring flowering response period: In Hyde Park, Canada, nearly 100% of plants flowered within 13 weeks after planting unrooted cuttings.

F. Outdoor flower production: The flower count in Hyde Park, Canada in 1986 was an average of 29 flowers per plant (range was 15–54) for June through September observed period. The wet summer was not ideal for flower production.

G. Durability: Minimum 10 days; shatter resistance good.

PLANT

A. Foliage:

*Form.*—5 lobed.

*Margin.*—Serrated.

*Color.*—The leaf has a white margin and a green 147B center. The intermediate zone between the edge and the center is approximately 147C.

*Tolerance of botrytis.*—Good.

B. General appearance and form:

*Internode length.*—21 mm.

*Branching pattern.*—Good; 3.25 branches per plant.

*Height.*—194 mm.

CHART A

| | PINK SILVER CROWN | PINK MINI CASCADE | PINK CASCADE |
|---|---|---|---|
| Corolla color | 55 A (top 2 petals) | 55 A top | 55 A top |
| | 54 B (bottom 3 petals) | 54 B bottom | 54 B bottom |
| Spring flowering response | 100% | 100% | 100% |
| Branching | 3.25 | 6.67 | 1.75 |
| Internode length | 20.58 mm | 14.92 mm | 35.08 mm |
| Leaf variegation | Yes | No | No |
| Umbel average diameter | 66.25 mm | 68.17 mm | 70.08 mm |
| Umbel average depth | 49.50 mm | 48.25 mm | 51.83 mm |
| Peduncle length | 106.42 mm | 90.67 mm | 116.58 mm |
| Pedicel length | 32.08 mm | 31.58 mm | 31.00 mm |
| Corolla average diameter | 39.42 mm | 37.08 mm | 38.75 mm |

I claim:

1. A new and distinct geranium plant named Pink Silver Crown, as described and illustrated, and particularly characterized by its pink flower color, variegated green and white leaves, short leaf internodes, good branching, and compact growth habit.

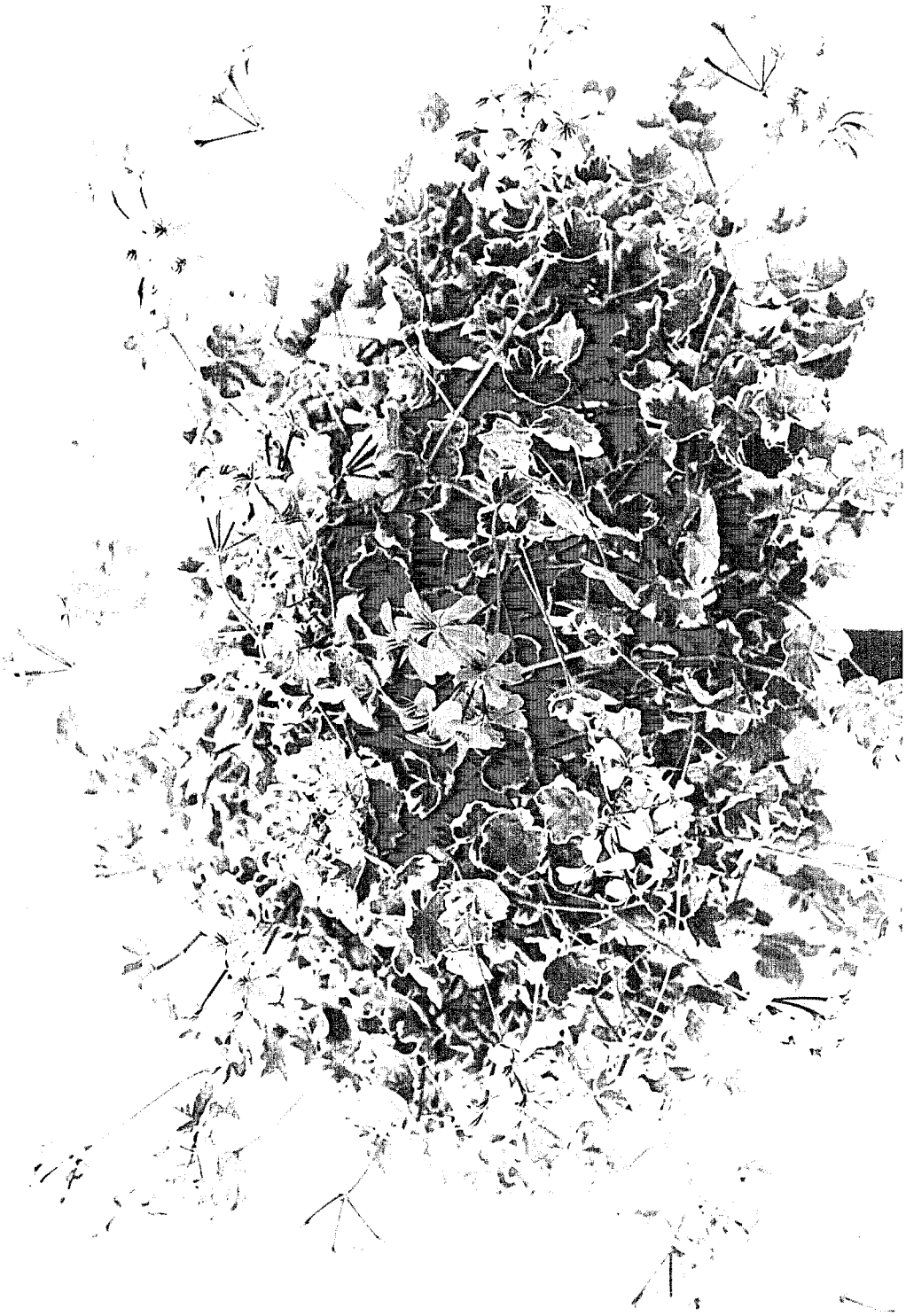

* * * * *